(12) United States Patent
Saleh

(10) Patent No.: US 11,090,347 B2
(45) Date of Patent: Aug. 17, 2021

(54) TECOMA PLANT BASED COMPOSITIONS FOR TREATING SKIN LESIONS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Ayman Mahmoud Saleh, Jeddah (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 16/560,123

(22) Filed: Sep. 4, 2019

(65) Prior Publication Data

US 2020/0085894 A1    Mar. 19, 2020

Related U.S. Application Data

(60) Provisional application No. 62/731,234, filed on Sep. 14, 2018.

(51) Int. Cl.
| | |
|---|---|
| *A61K 36/185* | (2006.01) |
| *A61K 9/00* | (2006.01) |
| *A61K 9/06* | (2006.01) |
| *A61P 35/00* | (2006.01) |
| *A61K 31/19* | (2006.01) |
| *A61K 47/20* | (2006.01) |
| *A61P 17/12* | (2006.01) |
| *A61K 31/191* | (2006.01) |

(52) U.S. Cl.
CPC .......... *A61K 36/185* (2013.01); *A61K 9/0014* (2013.01); *A61K 9/06* (2013.01); *A61K 31/19* (2013.01); *A61K 31/191* (2013.01); *A61K 47/20* (2013.01); *A61P 17/12* (2018.01); *A61P 35/00* (2018.01)

(58) Field of Classification Search
None
See application file for complete search history.

(56) References Cited

U.S. PATENT DOCUMENTS

| 8,597,695 | B1 | 12/2013 | Shraibom | |
| 8,790,727 | B2* | 7/2014 | West | A61P 19/02 |
| | | | | 424/777 |
| 2011/0206787 | A1 | 8/2011 | West et al. | |
| 2017/0239309 | A1 | 8/2017 | Mehra | |
| 2020/0247786 | A1* | 8/2020 | Saleh | A61P 35/02 |

FOREIGN PATENT DOCUMENTS

| BR | PI 0406051-2 A | 8/2006 |
| CN | 107405281 A | 11/2017 |

OTHER PUBLICATIONS

Govindappa M. et al. Antimicrobial Antioxidant Activity and Phytochemical Screening of Tecoma stans Juss ex Kunth. J of Phytology 3(3)68-76, 2011. (Year: 2011).*

Torane R. et al. Evaluation of Phenol and Flavonoid Content from Aerial Parts of Tecoma stans. Int J Pharmacy Pharmaceutical Sciences 3(Suppl 4)126-127, Sep. 2011. (Year: 2011).*

Evangeline, R. et al. In vitro Studies on Alpha-Glucosidase Inhibition, Antioxidant and Free Radical Scavenging Properties of Tecoma stans L. Int J Pharmacy Pharmaceutical Sciences 7(6)44-49 2015. (Year: 2015).*

Archana Singh, et al., "Tecoma stan: An Important Medicinal Plant", International Journal of Pharmaceutical Erudition, vol. 3, No. 2, Aug. 2013, pp. 13-21.

C. Das, et al., "Evaluation of Methanolic Bark Extract of *Tecoma stans* Linn, for Wound Healing in Albino Rats", International Journal of Pharmacy & Technology, vol. 2, Issue 3, Sep. 2010, pp. 735-742.

Maria Lysete A Bastos, et al., "Studies on the antimicrobial activity and brine shrimp toxicity of *Zeyheria tuberculosa* (Vell.) Bur. (Bignoniaceae) extracts and their main constituents", Annals of Clinical Microbiology and Antimicrobials, vol. 8, No. 16, May 18, 2009, pp. 1-6.

S. Kameshwaran, et al., "Wound Healing Potential of Ethanolic Extract of *Tecoma stans* Flowers in Rats", Pharmacologia, vol. 5, No. 6, 2014, pp. 215-221.

\* cited by examiner

*Primary Examiner* — Ralph J Gitomer
(74) *Attorney, Agent, or Firm* — Oblon, McClelland, Maier & Neustadt, L.L.P.

(57) ABSTRACT

A plant-based composition containing an alcohol extract of *Tecoma* species (e.g. *Tecoma stans*) and an exogenous carrier and/or excipient. Also provided is a composition including a mixture of three acids, namely corosolic acid, oleanolic acid, and ursolic acid, which can be found in the *Tecoma* species. Methods of treating skin lesions (e.g. warts, corns, calluses, and umbilical granulomas) and reducing symptoms associated with the skin lesions using such compositions are specified.

10 Claims, 10 Drawing Sheets

Before treatment 3-days post-treatment

TECOMA PLANT BASED COMPOSITIONS FOR TREATING SKIN LESIONS

CROSS REFERENCE TO RELATED APPLICATIONS

This application claims the benefit of priority of U.S. Provisional Application No. 62/731,234 filed Sep. 14, 2018, the entire contents of which are herein incorporated by reference.

BACKGROUND OF THE INVENTION

Technical Field

The present disclosure relates to a composition including an alcohol extract of *Tecoma* species and an exogenous pharmaceutically acceptable carrier and/or excipient. The present disclosure also relates to a composition containing a mixture of corosolic acid, oleanolic acid, and ursolic acid. These compositions are useful for treating superficial lesions including skin warts, calluses, corns, umbilical granuloma, and superficial basal cell carcinoma.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Conventional treatment of skin warts, calluses, and corns involves the use of keratolytic agents (e.g. salicylic acid), and/or other invasive medical procedures (e.g. cryosurgery, cryotherapy, and cauterization), which frequently leave scars in the treated skin area. In addition, there is no effective antiviral agent for curing skin lesions such as warts, which are caused by human papilloma virus (HPV). Physical removal of warts does not eradicate the causative virus. Therefore, recurrence rate of warts after clinical cure is often high due to virus reinfection.

Currently available medications for skin infections caused by HPV include Imiquimod (INN), which is a prescription drug acting as an immune response modifier. However, INN only shows limited effectiveness against the infection and cannot be used during pregnancy.

Traditional therapies for umbilical granuloma include topical application of a necrotic agent such as silver nitrate. However, large granulomas and those which do not respond to silver nitrate treatment may require invasive procedures including surgical excision.

Therefore, improved treatments for these skin lesions that do not involve an invasive procedure are still needed. In view of the forgoing, one objective of the present disclosure is to provide a composition with *Tecoma* plant extract. Another objective of the present disclosure is to provide a formulation containing a mixture of corosolic acid, oleanolic acid, and ursolic acid. The composition and the formulation are both effective for the treatment of skin lesions, in particular warts, corns, calluses, umbilical granulomas, and superficial basal cell carcinoma.

BRIEF SUMMARY OF THE INVENTION

A first aspect of the present disclosure relates to a plant-based composition that contains 1-500 g/L of an alcohol extract of at least one species of *Tecoma* relative to a total volume of the plant-based composition, and an exogenous pharmaceutically acceptable carrier and/or excipient which is not present in the at least one species of *Tecoma*, wherein the exogenous pharmaceutically acceptable carrier and/or excipient is an organic solvent, a cream base, or both, with the proviso that the organic solvent is not a polar protic solvent.

In one embodiment, the at least one species of *Tecoma* is selected from the group consisting of *Tecoma beckii*, *Tecoma capensis*, *Tecoma castanifolia*, *Tecoma cochabambensis*, *Tecoma fulva*, *Tecoma nyassae*, *Tecoma rosifolia*, *Tecoma stans*, *Tecoma tenuiflora*, and *Tecoma weberbaueriana*.

In one embodiment, the at least one species of *Tecoma* is *Tecoma stans*.

In one embodiment, the exogenous pharmaceutically acceptable carrier and/or excipient is the cream base, and the cream base comprises at least one selected from the group consisting of an emollient, an occlusive agent, and a thickener.

In one embodiment, the exogenous pharmaceutically acceptable carrier and/or excipient is DMSO.

In one embodiment, the alcohol extract of at least one species of *Tecoma* is sourced from a leaf, a stem, and/or a bark.

In one embodiment, the alcohol extract of at least one species of *Tecoma* is sourced from a leaf.

In one embodiment, the alcohol extract of at least one species of *Tecoma* is a methanol extract, an ethanol extract, or both.

In one embodiment, the plant-based composition contains 10-100 g/L of an alcohol extract of *Tecoma stans* relative to a total volume of the plant-based composition.

A second aspect of the present disclosure relates to a composition containing (i) corosolic acid, (ii) oleanolic acid, and (iii) ursolic acid, wherein a weight ratio of corosolic acid to oleanolic acid is in a range of 1:2 to 2:1, a weight ratio of corosolic acid to ursolic acid is in a range of 1:2 to 2:1, and a total weight of corosolic acid, oleanolic acid, and ursolic acid is at least 50 wt % relative to a total weight of the composition.

A third aspect of the present disclosure relates to a formulation involving the composition of the second aspect, and a pharmaceutically acceptable carrier and/or excipient, wherein corosolic acid, oleanolic acid, and ursolic acid are each present in an amount of 0.01-50 g/L relative to a total volume of the topical formulation.

In one embodiment, the pharmaceutically acceptable carrier and/or excipient includes DMSO.

A fourth aspect of the present disclosure relates to a method for treating a skin disease or condition. The method involves topically administering an effective amount of the plant-based composition of the first aspect onto a subject in need of therapy.

In one embodiment, the skin disease or condition is at least one selected from the group consisting of warts, corns, calluses, umbilical granulomas, and superficial basal cell carcinoma.

In one embodiment, the subject is administered with an effective amount of the plant-based composition 1 to 10 times daily for 1 to 30 consecutive days.

A fifth aspect of the present disclosure relates to a method for treating a skin disease or condition. The method involves topically administering an effective amount of the formulation of the third aspect onto a subject in need of therapy.

In one embodiment, the skin disease or condition is at least one selected from the group consisting of warts, corns, calluses, umbilical granulomas, and superficial basal cell carcinoma.

In one embodiment, the subject is administered with an effective amount of the formulation 1 to 10 times daily for 1 to 30 consecutive days.

A sixth aspect of the present disclosure relates to a personal care product containing the plant-based composition of the first aspect.

A seventh aspect of the present disclosure relates to a personal care product containing the composition of the second aspect.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
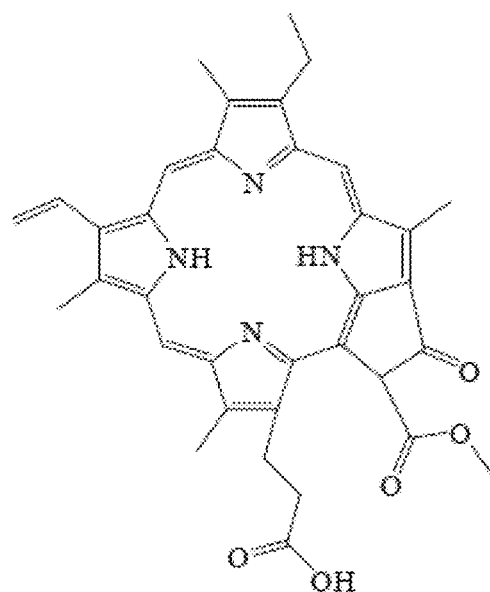
FIG. 1A shows the chemical structure of Pheophorbide-a identified in *Tecoma stans*.

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

The first aspect of the present disclosure relates to an plant-based composition, comprising, consisting essentially of, or consisting of: 1-500 g/L, 5-400 g/L, 10-300 g/L, 20-200 g/L, or 50-100 g/L of an alcohol extract of at least one species of *Tecoma* relative to a total volume of the plant-based composition, and an exogenous pharmaceutically acceptable carrier and/or excipient which is not present in the at least one species of *Tecoma*, wherein the exogenous pharmaceutically acceptable carrier and/or excipient is an organic solvent, a cream base, or both, with the proviso that the organic solvent is not a polar protic solvent.

As used herein, "plant" or "plant part" refers to any living organism of the kingdom Plantae and includes all plants described as grains, fruits and vegetables as well all plant parts or components including, but not limited to, roots, leaves, barks, branches, seeds, stems, stem shoots, bulbs, nuts, beans, grains, flowers, flower bud, pollen, vegetable skins, fruits and fruit skins during all periods of growth, preferably flowers, roots, barks, fruits, stems, and leaves during all periods of growth. Plant extracts, as defined herein, include solvent (e.g. aqueous and alcoholic) extracts obtained from any of the plant parts such as the flowers, roots, barks, fruits, stems, and leaves, as well as the whole plant. Extracts of *Tecoma stans* leaf are especially preferred.

The plant extract comprises phytochemicals and/or metabolites that include, without limitation, alkaloids, flavonoids, saponins, carbohydrates, polysaccharides, terpenoids (e.g., monoterpenoids and sesquiterpenoids), steroids, sterols, phenols, tannins, anthraquinones, anthocyanins, amino acids, proteins, and vitamins.

The at least one species of *Tecoma* may be *Tecoma beckii*, *Tecoma capensis*, *Tecoma castanifolia*, *Tecoma cochabambensis*, *Tecoma fulva*, *Tecoma nyassae*, *Tecoma rosifolia*, *Tecoma stans*, *Tecoma tenuiflora*, *Tecoma weberbaueriana*, or combinations thereof. Hybrid types such as *Tecoma* x *smithii* may be used as a species of *Tecoma*. A hybrid name contains "x" which links the parents of the hybrid. In at least one embodiment, the plant-based composition is substantially free of *Tecoma avellanedae*. *Tecoma avellanedae*, also referred to as *Handroanthus impetiginosus*, which belongs to a different genus than the *Tecoma* species of the present disclosure.

In a preferred embodiment, the at least one species of *Tecoma* is *Tecoma stans*. *Tecoma stans* (yellow bells, yellow trumpetbush) is a perennial shrub in the trumpet vine family that is cultivated as an ornamental plant. It has sharply toothed, lanceolate shaped, pinnate green leaves and bears large, showy, bright golden yellow trumpet-shaped flowers. The plant grows well in warm climates. Traditionally, *Tecoma stans* is known for its antidiabetic effects and is widely used in south America, southeast Asia, and the east coast of the United States for treating diabetes. A concentrated decoction of the flowers and leaves of *Tecoma stans* may be taken orally as an antidiabetic medication. In the Arabian Gulf peninsula, concentrated decoctions of the plant have been applied topically onto the skin for treating eczema. Extracts of *Tecoma stans* have been tested for their anti-proliferative, antioxidant, anti-inflammatory, central analgesic, anti-nociceptive, antispasmodic, cardioprotective, antimicrobial (e.g. antibacterial, antifungal), insecticidal, wound healing, antidiabetic, nephroprotective and hepatoprotective effects as well as gastric ulcer healing properties [Amad M al-Lazzari (2012); Genotoxic and Cytotoxic study of *Tecoma stans* Bignoniaceae; Pakistan journal of biological sciences; Vol. 15 No. 2; 92-97; Anburaj G., Marimuthu M. and Manikandan R (2016); In vitro antimicrobial activity of aqueous and Ethanol extracts of *Tecoma stans* bark against pathogenic Bactria; International Recent Research Journal on Science and Technology; Vol. 8 No. 2; 26-28; Anburaj G., Marimuthu M., Rajasudha V. and Manikandan R (2016); Phytochemical screening and GC-MS analysis of ethanolic extract of *Tecoma stans* (Family: Bignoniaceae) Yellow Bell Flowers; Journal of Pharmacognosy and Phytochemistry; Vol. 5 No. 4; 172-175; Anburaj G., Marimuthu M., Sobiyana P. and Manikandan R. (2016); A Review on *Tecoma stans*; International Journal of Engineering Research and Modern Education; Vol. 1 No. 1; 43-49; Arnabaditya Mohanty, Vinod Kumar Sahu, Ashutosh Mishra, Dusmanta Kumar Pradhan and Manas Ranjan Mishra (2012); Gastric ulcer healing activity of *Tecoma stans* Leaf; International Research Journal of Pharmaceutical Sciences; Vol. 3 No. 1; 32-33; Boopathi T., Gopalasatheeskumar K., Parthiban S., Sangeetha G., Thanga Kokila M. and Manimaran T (2017); Evaluation of Antimicrobial Activity of *Tecoma stans* and Muntingia calabura; World Journal of Pharmaceutical Research; Vol. 6 No. 3; 617-627; Brahmam B., Sirisha K., Sathish Kumar M., Narendra Babu A. and Rama Rao N. V (2015); Evaluation of Central Analgesic Activity of *Tecoma stans* Flower Extracts; Vol. 4 No. 1; 89-92; Brahmam B., Sirisha K., Sathish Kumar M., Narendra Babu A., Rama Rao N. V. and Rama Rao N (2015); Evaluation of Anti-inflammatory Activity of Flower Extracts of *Tecoma stans* on Carrageenan-Induced Paw oedema in Rats by Using Digital Plethysmometer; Research Journal of Pharmaceutical, Biological and Chemical Sciences; Vol. 6 No. 5; 641-644; Chaugan S. V. S., Jolly Singh and Satoshi Tahara (2004); Role of phenolic sans boron in reproductive success in seasonally transient sterile *Tecoma stans* L; Indian journal of experimental biology; Vol. 42 No. 1; 197-201; Das C., Dash S., Sahoo D. C. and Mohanty A (2010); Evaluation of Methanolic Bark Extract of *Tecoma stans* Linn, for Wound Healing in Albino Rats; International Journal of Pharmacy and Technology; Vol. 2 No. 3; 735-742; Divya Sri G., Narendra Babu A., Sathish Kumar M., Venkateswarlu V. and Ashok Kumar K (2014); Pharmacognostical Characteristics and Medicinal Uses of *Tecoma stans*: A Review; Journal of Medical and Pharmaceutical Innovation; Vol. 1 No. 2; 1-4; Gharib Naseri M. K., Asadi Moghaddam M. and Bahadoram S (2007); Antispasmodic effect of *Tecoma stans* (L.) Juss leaf extract on rat ileum; DARU; Vol. 15 No. 3; 123-128; Govindappa M., Sadananda T. S., Channabasava R. and Vinay B Raghavendra (2011); In vitro Anti-Inflammatory, Lipoxygenase, Xanthine Oxidase and Acetylcholinesterase Inhibitory Activity of *Tecoma stans* (L.) Juss. Ex Kunth; International Journal of Pharma and Bio Sciences; Vol. 2 No. 2; 275-285; Govindappa M., Sadananda T. S., Channabasava R., Jeevitha M. K., Pooja K. S., Vinay B. and Raghavendra (2011) Antimicrobial, Antioxidant Activity and Phytochemical Screening of *Tecoma stans* (L.) Juss. Ex Kunth; Journal of Phytology Phyto-pharmacology; Vol. 3 No. 3; 68-76; Indra Gandhi M. and Ramesh S (2010); Antifungal and hemolytic activities of organic extracts of *Tecoma stans* (Bignoniaceae); Journal of Ecobiotechnology; Vol. 2 No. 2; 26-32; Kameshwaran S., Senthilkumar R., Thenmozhi S. and Dhanalakshmi M (2014); Wound healing potential of ethanolic extract of *Tecoma stans* flowers in rat; Pharmacologia; Vol. 1 No. 1; 215-221; Kameshwaran S., Sundaraganapathy R., Thenmozhi S., Dhanalakshmi M., Vasuki K. and Manjuladevi K (2014); *Tecoma stans* protect Central Nervous System Against Oxidative Damages of Electromagnetic Radiation on Rat; Acta Biomedica Scientia; Vol. 1 No. 1; 40-44; Kameshwaran S., Suresh V., Arunachalam G., Kanthlal S. K. and Mohanraj M (2012); In vitro and in vivo anti-cancer activity of methanolic extract of *Tecoma stans* flowers; International research journal of pharmacy; Vol. 3 No. 3; 246-251; Kamilia F. Taha, El-sayeda A. El-kashoury, Shahira M. Ezzat and Naglaa A. Saleh (2016); Antimicrobial and antioxidant activity of volatile constituents of the leaves of *Tecoma Smithii* Will Wats; Global Journal of Medicinal Plant Research; Vol. 4 No. 4; 16-22; Kottai Muthu A., Borse L. B., Thangatripathi A. and Borse S. L (2012); Antioxidant activity of heartwood of *Tecoma stans*. (L) Juss. Ex Kunth; Journal of Pharmacy Research; Vol. 5 No. 2; 896-898; Kottai Muthu A., Laxmikant B. Borse, Thangatripathi A. and Sandhya L. Borse (2012); Antimicrobial Activity of Heartwood of *Tecoma stans*; International Journal of Pharmacy and Pharmaceutical Sciences; Vol. 4 No. 3; 384-386; Lakshmi Prasanna V., Lakshman K., Medha M. Hegde and Vinutha Bhat (2013); Antinociceptive and Anti-Inflammatory activity of *Tecoma stans* Leaf Extracts; Indian Journal of Research in Pharmacy and Biotechnology; Vol. 1 No. 2; 156-160; Mohamed Abdel-Hamid Taher, Dawood Hosni Dawood, Mostafa Ibrahim Sanad and Ramadan Ahmed Hassan (2016); Searching for anti-hyperglycemic phytomolecules of *Tecoma stans*; European Journal of Chemistry; Vol. 7 No. 4; 397-404; Name H. and Minal Wani (2014); Callus Induction Studies and Active Components and Antioxidant Activity Investigation from Leaves and Callus of *Tecoma stans* L. Juss. Ex Kunth; Research Journal of Pharmaceutical, Biological and Chemical Sciences; Vol. 5 No. 2; 604-610; Rajamurugan R., Thirunavukkarasu C., Sakthivel V., Sivashanmugam M. and Raghavan C. M (2013); Phytochemical Screening, Antioxidant and Antimicrobial Activities of Ethanolic Extract of *Tecoma stans* Flowers; Int J Pharm Bio Sci.; Vol. 4 No. 2; 124-130; Raju S., Kavimani S., Uma Maheshwara Rao V. and Sreeramulu Reddy K (2011); *Tecoma stans* (L.) Juss. ex Kunth (Bignoniaceae): Ethnobotany, Phytochemistry and Pharmacology; Journal of Pharmaceutical and Biomedical Sciences; Vol. 8 No. 7; 1-5; Ramesh T., Anusha V. and Ravi Kumar (2009); Antibacterial Activity of Methanolic Extract of Roots of *Tecoma stans*; Int. J. Chem. Sci.; Vol. 7 No. 1; 6-8; Senthilkumar C. S., Suresh Kumar M. and Rajasekara Pandian M (2010); In vitro Antibacterial Activity of Crude Leaf Extracts from *Tecoma stans* (L) Juss. Et Kunth, *Coleus Forskohlii* and Pogostemon Patchouli against Human Pathogenic Bacteria; International Journal of PharmTech Research; Vol. 2 No. 1; 438-442; Shanmukha I., Abubaker Siddiq, Prabhu K. and Ramachandra Setty S (2012); Effect of *Tecoma stans* Leaves Extract on Experimentally Induced Renal Injury In Various Animal Models; Am. J. PharmTech Res.; Vol. 2 No. 6; 800-809; Shanmukha I., Vijay Kumar M. and Ramachandra Setty S (2013); Effect of *Tecoma stans* Leaves for its Preventive Role on Experimentally Induced Liver Toxicity; International Journal of Pharm Tech Research; Vol. 5 No. 3; 915-923; Shanmukha I., Vijay Kumar M. and Ramachandra Setty S (2014); Cardioprotective effect of hydroalcoholic extract of *Tecoma stans* flowers against isoproterenol-induced myocardial infarction in rats; Asian Pac J Trop Dis.; Vol. 4 No. 1; 378-384; Sridharan G., Sarvanan R. and Brindha P (2014); Evaluation of Anticancer Potentials of *Tecoma stans* (L). Juss. Ex. Kunth against EAC Cell Lines; International Journal of Pharmacy and Pharmaceutical Sciences; Vol. 6 No. 1; 88-92; Subalakshmi T. and Jepa Chandra Mohan (2017); Inhibitory Effect of Different Solvent Extracts of *Tecoma stans, Ixora Coccinea* and Aerva Lenata Leaves on *Pseudomonas aeruginosa* and *Streptococcus* Sp. of cattle Pathogens; World Journal of Pharmacy and Pharmaceutical Sciences; Vol. 6 No. 2; 1219-1228; Sundas Iltaf, Zaheer-Ud-Din Khan, Rizwana Rafique and Anjum Parveen (2016); Evaluation of antibacterial activity of leaf extracts of Mansoa alliacea (Lam.), *Tecomaria capensis* (Thunb.) Spach and *Tecoma stans* (L.) Juss. Ex; Journal of Biodiversity and Environmental Sciences; Vol. 9 No. 1; 69-75; Sunitha Katta, Ganapathy Seru and Sridhar Y (2016); Constituents from the Leaves of *Tecoma stans* Juss; World Journal of Pharmaceutical Sciences; Vol. 4 No. 12; 272-274; Sunita Verma (2016); Phytochemical and pharmacological review study on *Tecoma stans* Linn; Journal of Medicinal Plants Studies; Vol. 4 No. 5; 162-164; Tavs A. Abere and Comfort O. Enoghama (2015); Pharmacognostic standardization and insecticidal activity of the leaves of *Tecoma stans* Juss (Bignoniaceae); Journal of Science and Practice of Pharmacy; Vol. 2 No. 1; 39-45; and Thirumal M., Kishore G. and Surya Srimanthula (2013); Anti-Proliferative Activity of Various Parts of *Tecoma stans* (L.) Against Human Breast Cancer Cells In vitro; Research Journal of Pharmaceutical, Biological, and Chemical Sciences; Vol. 4 No. 2; 305-313].

The alcohol extract of *Tecoma* may be sourced from a leaf, a stem, a bark, or combinations thereof. Preferably, the alcohol extract of *Tecoma* is sourced from a leaf. In some embodiments, the alcohol extract of *Tecoma* is not sourced from a flower, a root, and a fruit. As discussed in Example 1, extracts from the flower, the root, and the fruit from *Tecoma stans* exhibited much lower therapeutic effect than that from the leaf.

Exemplary alcohols include, but are not limited to, methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol, and polyols (e.g. propylene glycol, polyethylene glycol, glycerol, and poly(tetramethylene ether) glycol).

In some embodiments, the alcohol extract of *Tecoma* is a methanol extract, an ethanol extract, an n-propanol extract, an isopropanol extract, an n-butanol extract, or mixtures thereof. In a preferred embodiment, the alcohol extract of *Tecoma* is a methanol extract, an ethanol extract, or both. Most preferably, the alcohol extract of *Tecoma* is a methanol extract. In certain embodiments, other solvents including, but not limited to, water, acetone, acetonitrile, tetrahydrofuran (THF), 1,4-dioxane, dichloromethane, chloroform, ethyl acetate, pet ether, pentane, hexane(s), may be used in addition to or in lieu of the alcohol to extract the *Tecoma*.

Solvent extraction methods of plants are known to those of ordinary skill in the art. For example, the alcohol extracts of the present disclosure may be prepared as follows. The plant part(s) of interest may be collected and then washed thoroughly, preferably twice/thrice with tap water, to remove both epiphytes and necrotic plants; preferably followed by washing with sterile distilled water to remove associated debris if any. The clean and fresh plant parts may be sun-dried or dried in the shade for 5-60 days, preferably 10-40 days, or about 30 days, and then finely cut, or preferably powdered/pulverized. The dried finely cut or powdered plant parts may be mixed and extracted with the alcohol (e.g., methanol) in an amount of 0.001-5 g/mL, 0.01-3 g/mL, 0.02-2 g/mL, or 0.1-1 g/mL of the alcohol at a temperature of 10-50° C., 15-40° C., or 20-30° C. for 0.5-30 days, preferably 1-20 days, more preferably 5-10 days. The resulting infusion is then preferably filtered thoroughly until no insoluble material appears in the alcohol extract to obtain a diluted alcohol extract. The diluted alcohol extract may be concentrated via evaporation of the alcohol by heating under standard pressure, drying under vacuum, and/or using a rotary evaporator. In some embodiments, the alcohol content of the alcohol extract of *Tecoma* is less than 10 wt %, preferably less than 5 wt %, more preferably less than 2 wt %, relative to a total weight of the alcohol extract.

Figure 1B:
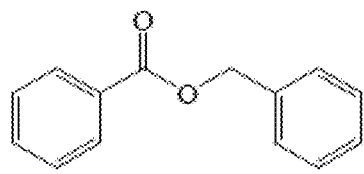
FIG. 1B shows the chemical structure of benzylbenzoate identified in *Tecoma stans*.
Figure 1C:
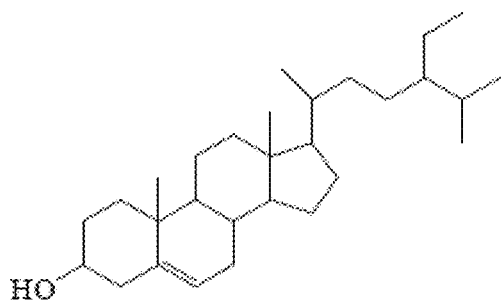
FIG. 1C shows the chemical structure of β-sitosterol identified in *Tecoma stans*.
Figure 1D:
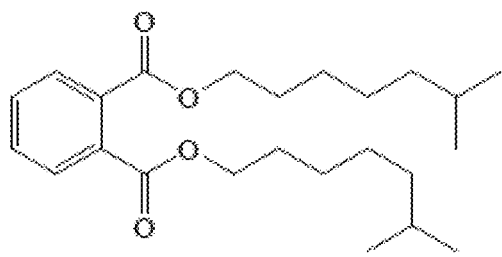
FIG. 1D shows the chemical structure of diisooctyl phthalate identified in *Tecoma stans*.
Figure 1E:
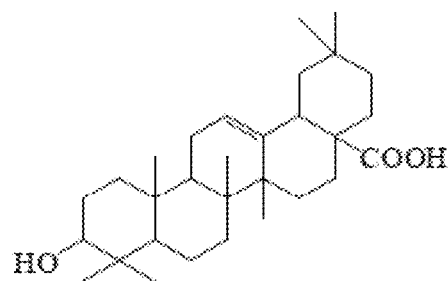
FIG. 1E shows the chemical structure of oleanolic acid identified in *Tecoma stans*.
Figure 1F:
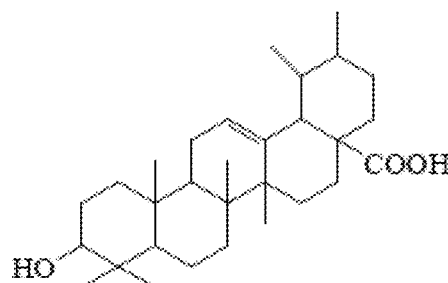
FIG. 1F shows the chemical structure of ursolic acid identified in *Tecoma stans*.
Figure 1G:
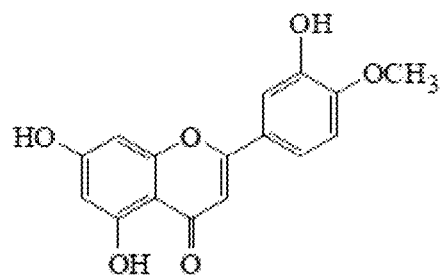
FIG. 1G shows the chemical structure of luteolin 4'-methyl ether identified in *Tecoma stans*.
Figure 1H:
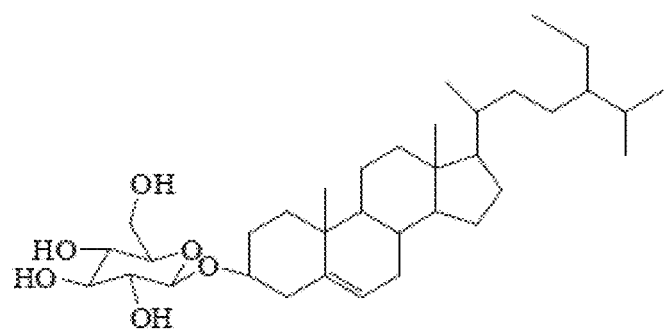
FIG. 1H shows the chemical structure of β-sitosteryl glucoside identified in *Tecoma stans*.
Figure 1I:
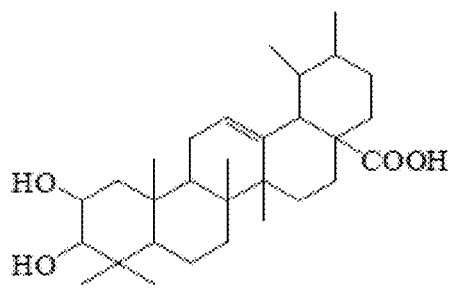
FIG. 1I shows the chemical structure of corosolic acid identified in *Tecoma stans*.
Figure 1J:
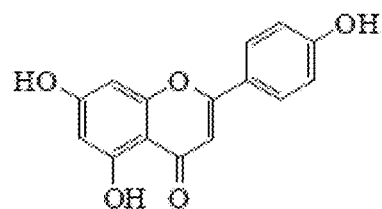
FIG. 1J shows the chemical structure of apigenin identified in *Tecoma stans*.
Figure 1K:
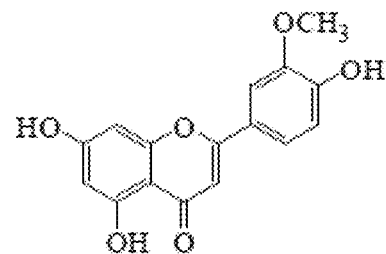
FIG. 1K shows the chemical structure of luteolin 3'-methyl ether identified in *Tecoma stans*.
Figure 1L:
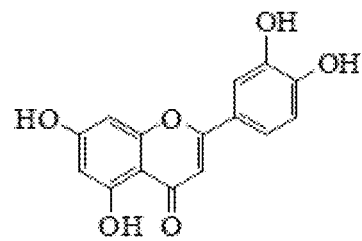
FIG. 1L shows the chemical structure of luteolin identified in *Tecoma stans*.
Figure 1M:
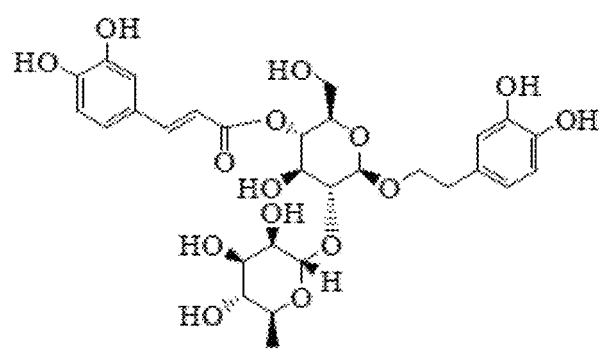
FIG. 1M shows the chemical structure of acteoside identified in *Tecoma stans*.
Figure 1N:
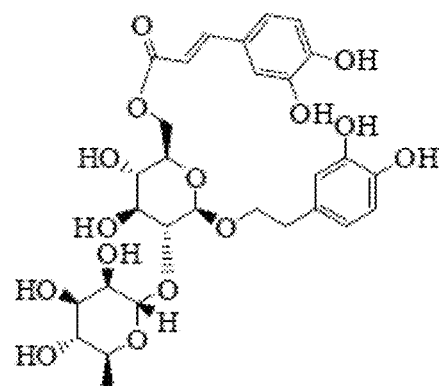
FIG. 1N shows the chemical structure of isoacteoside identified in *Tecoma stans*.
Figure 2A:
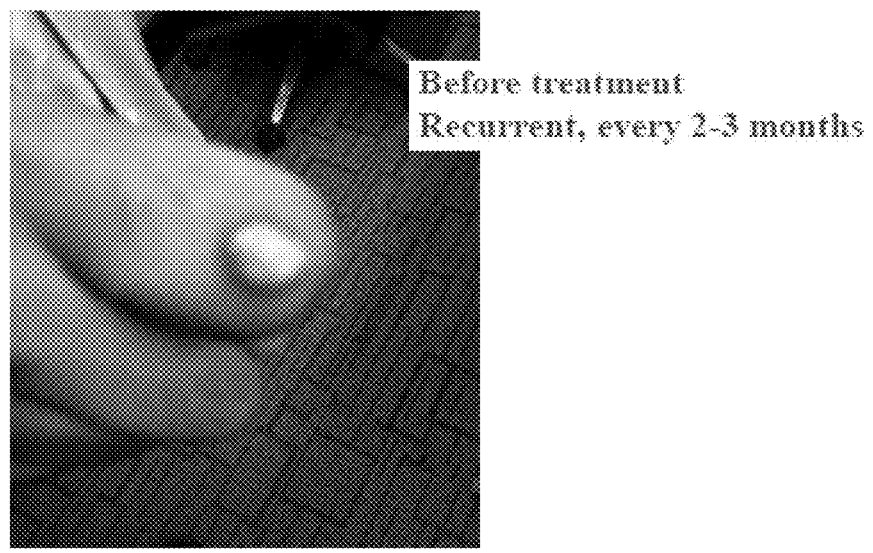
FIG. 2A is a picture showing untreated human skin having warts.
Figure 2B:
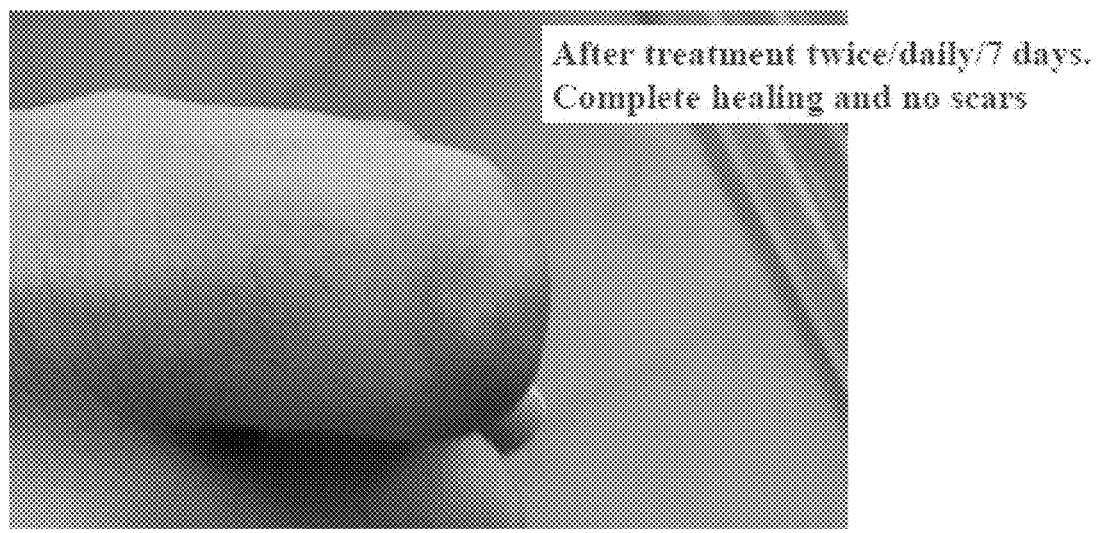
FIG. 2B is a picture showing the human skin of FIG. 2A after treatment with a methanol extract of *Tecoma stans* twice daily for 7 days.
Figure 2C:
FIG. 2C is a picture showing the human skin of FIG. 2A 1 year after treatment with a methanol extract of *Tecoma stans* twice daily for 7 days.

The alcohol extract of the at least one species of *Tecoma* may comprise macrocyclic compounds including Pheophorbide-a (FIG. 1A), pentacyclic triterpenoids including oleanolic acid (FIG. 1E), ursolic acid (FIG. 1F), and corosolic acid (FIG. 1I), esters including benzylbenzoate (FIG. 1B), and diisooctyl phthalate (FIG. 1D), phytosterols and derivatives thereof including β-sitosterol (FIG. 1C), and β-sitosteryl glucoside (FIG. 1H), flavonoids including luteolin (FIG. 1L), luteolin 4'-methyl ether (FIG. 1G), luteolin 3'-methyl ether (FIG. 1K), apigenin (FIG. 1J), as well as caffeoyl phenylethanoid glycosides including acteoside (verbascoside) (FIG. 1M), and andisoacteoside (FIG. 1N).

In some embodiments, the plant-based composition contains 0.1-500 g/L of the alcohol extract of at least one species of *Tecoma* relative to a total volume of the plant-based composition, preferably 0.5-400 g/L, preferably 1-300 g/L, preferably 5-200 g/L, preferably 10-100 g/L, preferably 15-80 g/L, preferably 20-60 g/L, preferably 30-50 g/L of the alcohol extract of at least one species of *Tecoma* relative to a total volume of the plant-based composition. In a preferred embodiment, the plant-based composition contains 0.1-500 g/L of the alcohol (e.g. methanol) extract of *Tecoma stans* relative to a total volume of the plant-based composition, preferably 0.5-400 g/L, preferably 1-300 g/L, preferably 5-200 g/L, preferably 10-100 g/L, preferably 15-80 g/L, preferably 20-60 g/L, preferably 30-50 g/L of the alcohol extract of *Tecoma stans* relative to a total volume of the plant-based composition.

The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

As used herein, the term "pharmaceutically acceptable" refers to counter-ions, compounds, materials, ingredients, compositions, and/or dosage forms which are, within the scope of sound medical judgement, suitable for use in contact with the tissues (e.g. skin) of human beings and animals without excessive toxicity, irritation, allergic response, or other problem or complication, commensurate with a reasonable benefit/risk ratio.

The plant-based composition further comprises an exogenous pharmaceutically acceptable carrier and/or excipient which is not present in the at least one species of *Tecoma*. The exogenous pharmaceutically acceptable carrier and/or excipient may be an organic solvent that is not a polar protic solvent, a cream base, or both. When present, the cream base may contain at least one selected from the group consisting of an emollient, an occlusive agent, and a thickener. The following carriers and excipients are not found in *Tecoma*.

Exemplary organic solvent that may be applicable to the present disclosure include, but are not limited to, alkyl methyl sulfoxide (e.g., dimethyl sulfoxide (DMSO), decylmethyl sulfoxide, tetradecylmethyl sulfoxide), glycol ethers (e.g. 1,2-dimethoxyethane, diglyme, triglyme), ketones (e.g., acetone, butanone), esters (e.g. ethyl acetate, propyl acetate), an amide/lactam (e.g. dimethylformamide, dimethylacetamide, N-methyl-2-pyrrolidone), acetonitrile, propionitrile, butyronitrile, benzonitrile, ethylene carbonate, propylene carbonate, 1,3-dimethyl-3,4,5,6-tetrahydro-2 (1H)-pyrimidinone, pentane, hexane, heptane, diethyl ether, 1,4-dioxane, and mixtures thereof. In at least one embodiment, the organic solvent is not a polar protic solvent such as methanol, ethanol, n-propanol, isopropanol, and n-butanol.

In a preferred embodiment, the exogenous pharmaceutically acceptable carrier and/or excipient is dimethyl sulfoxide (DMSO). DMSO is a versatile substance that has numerous pharmaceutical and cosmetic uses. For example, DMSO may be effective in boosting tissue (e.g. skin) penetration of other substances it carries, especially other therapeutically active ingredient, and thus accelerate delivery and assimilation of a pharmaceutical/cosmetic composition into the tissue. If present, DMSO may be present in the plant-based composition in an amount of 1-1,000 g/L, 10-750 g/L, 25-500 g/L, 50-250 g/L, or 100-200 g/L.

An emollient may attract and hold water in the stratum corneum and epidermis after topic application of the plant-based composition. Exemplary emollients include, without limitation, urea, aloe vera gel, an α-hydroxy acid (e.g., lactic acid), glyceryl triacetate, a polymeric polyol (e.g., polydextrose), a sugar alcohol (e.g., glycerol/glycerin, sorbitol, xylitol, and maltitol), a PEG-20 almond glyceride, Glucam P-20, Glucam E-10, Glucam P-10, Glucam E-20, Glucam P-20 distearate, cetyl acetate, acetylated lanolin alcohol (e.g., acetulan), cetyl ether (e.g., PPG-10), myristyril ether (e.g., PPG-3), hydroxylated milk glycerides (e.g., Cremeral HMG), polyquaternium compounds (e.g., U-care compounds), copolymers of dimethyl dialyl ammonium chloride and acrylic acid (e.g., Merquat), dipropylene glycol methyl ethers (e.g., Dowanol DPM, Dow Corning), and polypropylene glycol ethers (e.g., Ucon 50-HB-600, Union Carbide). Other suitable emollients may include hydrocarbon-based emollients, such as petrolatum or mineral oil; fatty ester-based emollients, such as methyl, isopropyl and butyl esters of fatty acids (e.g., isopropyl palmitate, isopropyl myristate, isopropyl isostearate, diisopropyl sebacate); and $C_{12}$-$C_{16}$ fatty alcohol lactates, such as cetyl lactate and lauryl lactate. Additional fatty ester-based emollients include isostearyl isostearate, propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter. If present, the emollient may be present in the plant-based composition in an amount of 1-100 g/L, 5-80 g/L, 10-60 g/L, or 15-30 g/L.

An occlusive agent may help create a semi-occlusive film on skin after topical application which can help form a barrier to inhibit evaporative loss of moisture from the body and protect the skin from environmental irritants. Exemplary occlusive agents include, but are not limited to, dimethicone, cyclomethicone, trimethylsiloxysilicate, and petrolatum. If present, the occlusive agent may be present in the plant-based composition in an amount of 1-100 g/L, 5-80 g/L, 10-60 g/L, or 15-30 g/L.

A thickening agent may assist in adjusting/enhancing the viscosity of the plant-based composition. Certain thickening agents may also function as stabilizers to maintain the stability of an emulsion. Exemplary thickening agents include, but are not limited to, polyacrylamide polymers, polysaccharides, natural or synthetic gums, such as methyl hydroxypropyl cellulose, xanthan gum, polysaccharide gum, hydroxyl propyl cellulose, hydroxyl propyl methyl cellulose, and hydroxyl ethyl cellulose. Some emollients, such as petrolatum, may also function as a thickening agent. If present, the thickening agent may be present in the plant-based composition in an amount of 0.1-50 g/L, 0.5-25 g/L, 1-10 g/L, or 2-5 g/L.

In some embodiments, the plant-based composition further comprises an emulsifier. Useful emulsifiers include ethoxylated fatty alcohols, ethoxylated fatty acids, partial glycerides of ethoxylated fatty acids, polyglycerolated fatty acid triglycerides and ethoxylated derivatives thereof, and mixtures thereof. Exemplary emulsifiers include, but are not limited to, glyceryl stearate, cetyl alcohol, behenyl alcohol, cetearyl alcohol, stearic acid, and emulsifying waxes (e.g. Incroquat and Polawax). Surfactants may act as emulsifiers. Surfactants that may be present in the plant-based compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltri methyl ammonium bromide, dodecyltrim ethyl ammonium bromide, tetradecyltrimethylammonium bromide, tetradecyltrimethyl-ammonium chloride, and dodecylammonium chloride, and combinations thereof. If present, the emulsifier may be present in the plant-based composition in an amount of 1-100 g/L, 5-80 g/L, 10-60 g/L, or 15-30 g/L.

In some embodiments, the plant-based composition further comprises water, and/or an organic solvent in the cream base. Exemplary organic solvents include, without limitation, ethers (e.g. diethyl ether, dibutyl ether, tetrahydrofuran, 1,4-dioxane, tetrahydropyran, t-butyl methyl ether, cyclopentyl methyl ether, di-iso-propyl ether), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), hydrocarbons (e.g., cyclohexane, hexane, isooctane, n-pentane), chlorinated solvents (dichloromethane, chloroform, carbon tetrachloride, perchloroethylene (tetrachloroethylene), 1,1,2,2-tetrachloroethane, 1,1,2-trichloroethane, trichloroethylene, methyl chloroform (1,1,1-trichloroethane), 1,2,3-trichloropropane, ethylene dichloride, 1,2-dichloropropane (propylene dichloride), 1,2-dichloroethylene, 1,1-dichloroethane, chlorobenzene), alkyl methyl sulfoxide (e.g., dimethyl sulfoxide (DMSO), decylmethyl sulfoxide, tetradecylmethyl sulfoxide), glycol ethers (e.g. 1,2-dimethoxyethane, diglyme, triglyme), ketone (e.g., acetone, butanone), esters (e.g. ethyl acetate, propyl acetate), an amide/lactam (e.g. dimethylformamide, dimethylacetamide, pyrrolidone, N-methyl-2-pyrrolidone, N-(2-hydroxyethyl) pyrrolidone), acetonitrile, propionitrile, butyronitrile, benzonitrile, ethylene carbonate, propylene carbonate, 1,3-dimethyl-3,4,5,6-tetrahydro-2(1H)-pyrimidinone, and mixtures thereof.

The plant-based composition may be suitable for topical application. The plant-based composition intended for topical application can be produced in liquid or semi-solid formulation. The composition may be in a form of a salve, a lotion, a cream, an ointment, a solution, an emulsion, a suspension, a gel (e.g., a cream gel or a hydrogel), or a suspension/dispersion. In other embodiments, the composition may be in a form of a multiple emulsion, such as oil and/or silicone in water emulsions, water-in-oil and/or silicone emulsions, water/oil/water or water/silicone/water type emulsions, and oil/water/oil or silicone/water/silicone type emulsions. The composition may be a leave-on type or a rinse-off type.

In some embodiments, the plant-based composition may be formulated for administration by mouth. Solid dosage forms for oral administration can include capsules, tablets, pills, powders, and granules. Liquid dosage forms for oral administration can include pharmaceutically acceptable emulsions, solutions, suspensions, syrups, and elixirs containing inert diluents commonly used in the art, such as water.

The plant-based composition may be prepared by mixing the aforementioned alcohol extract of at least one species of *Tecoma* and the exogenous pharmaceutically acceptable carrier and/or excipient such as DMSO, and/or the cream base (e.g. the emollient, the occlusive agent, the thickener, the emulsifier) simultaneously or sequentially. The mixing process may be performed in any conventional vessel with adequate agitation. In some embodiment, mixing is performed in a high speed double-mounted turbine dissolver. Methods of agitation include, but are not limited to, using a propeller, using an agitator, a vortexer, a rotary shaker, a magnetic stirrer, an overhead stirrer, a sonicator (e.g. an ultrasonic bath, an ultrasonic probe), and a pump.

A further aspect of the present disclosure relates to a composition comprising, consisting essentially of, or consisting of: (i) corosolic acid, (ii) oleanolic acid, and (iii) ursolic acid. A total weight of corosolic acid, oleanolic acid, and ursolic acid is at least 50 wt %, preferably at least 60 wt %, preferably at least 75 wt %, preferably at least 80 wt %, preferably at least 90 wt %, preferably at least 95 wt %, preferably at least 98 wt %, preferably at least 99 wt %, relative to a total weight of the composition. The composition of the present disclosure may be considered as a "concentrate" of the three acids (i.e. corosolic acid, oleanolic acid, ursolic acid).

In one embodiment, a weight ratio of corosolic acid to oleanolic acid is in a range of 1:2 to 2:1, preferably 2:3 to 3:2, more preferably about 1:1. In a related embodiment, a weight ratio of corosolic acid to ursolic acid is in a range of 1:2 to 2:1, preferably 2:3 to 3:2, more preferably about 1:1.

The present disclosure is further intended to include compositions that contain single compound, or up to two compounds selected from the group consisting of (i) corosolic acid, (ii) oleanolic acid, and (iii) ursolic acid. For example, the composition may only contain corosolic acid, oleanolic acid, or ursolic acid in an amount of at least 50 wt %, preferably at least 60 wt %, preferably at least 75 wt %, preferably at least 80 wt %, preferably at least 90 wt %, preferably at least 95 wt %, preferably at least 98 wt %, preferably at least 99 wt %, relative to a total weight of the composition. Alternatively, the composition may contain a mixture of corosolic acid and oleanolic acid, a mixture of oleanolic acid and ursolic acid, or a mixture of corosolic acid and ursolic acid in a ratio as previously specified, and in an amount of at least 50 wt %, preferably at least 60 wt %, preferably at least 75 wt %, preferably at least 80 wt %, preferably at least 90 wt %, preferably at least 95 wt %, preferably at least 98 wt %, preferably at least 99 wt %, relative to a total weight of the composition.

Triterpenes are a class of chemical compounds composed of three terpene units with the molecular formula $C_{30}H_{48}$. Triterpenoids are functionalized triterpenes having heteroatoms. Triterpenoids with several pentacyclic motifs may possess potential biological and medicinal effects. Exemplary triterpenoids include, but are not limited to, oleanolic acid, ursolic acid, betulinic acid, moronic acid, curcurbitacins, lupeol, and corosolic acid.

Corosolic acid (FIG. 1i, (2α,3β)-2,3-dihydroxyurs-12-en-28-oic acid, 2α-hydroxyursolic acid) is a pentacyclic triterpene acid isolated from the leaves of *Lagerstroemia speciosa*. *Lagerstroemia Speciosa* is commonly known as Crepe Myrtle and belongs to the botanical family lythraceae. It is a very common ornamental deciduous tree that grows in the tropical areas of the globe. Corosolic acid has also been found in other plants such as *Vaccinium macrocarpon* (cranberry), *Ugni molinae*, *Eriobotrya japonica*, *Perilla frutescens*, *Weigela subsessilis*, *Glechoma longituba*, *Potentilla chinensis*, *Rubus biflorus*, and *Phlomis umbrosa*. Corosolic acid has been previously studied for its use for controlling blood sugar levels and treating diabetes. In some embodiments, the corosolic acid of the present disclosure is sourced from at least one species of *Tecoma*, preferably from *Tecoma stans*. Alternatively, corosolic acid may be commercially available from vendors such as Sigma-Aldrich.

Figure 3A:
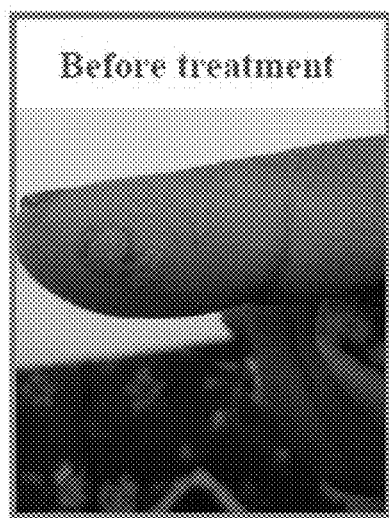
FIG. 3A is a picture showing untreated human skin having warts.
Figure 3B:
FIG. 3B is a picture showing the human skin of FIG. 3A 3 days after treatment with a mixture of corosolic acid, oleanolic acid, and ursolic acid twice daily.
Figure 3C:
FIG. 3C is a picture showing the human skin of FIG. 3A 7 days after treatment with a mixture of corosolic acid, oleanolic acid, and ursolic acid twice daily.
Figure 4A:
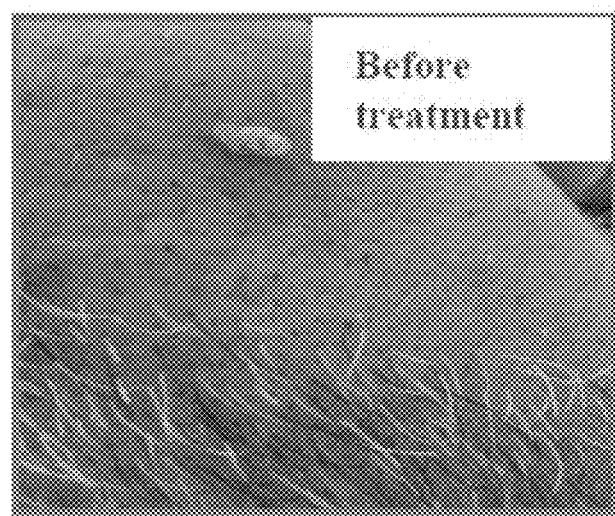
FIG. 4A is a picture showing untreated human skin having warts.
Figure 4B:
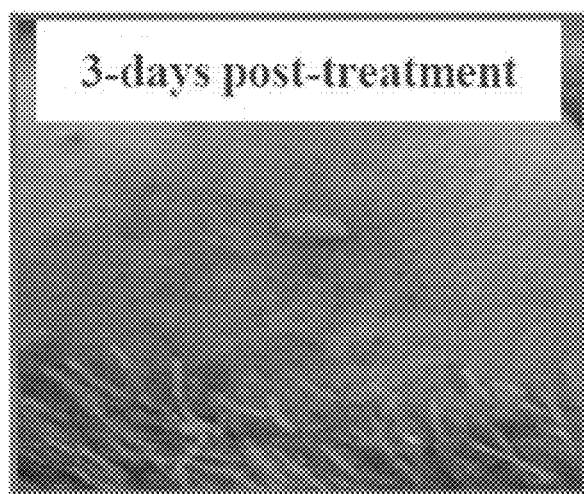
FIG. 4B is a picture showing the human skin of FIG. 4A 3 days after treatment with a mixture of corosolic acid, oleanolic acid, and ursolic acid twice daily.
Figure 4C:
FIG. 4C is a picture showing the human skin of FIG. 4A 5 days after treatment with a mixture of corosolic acid, oleanolic acid, and ursolic acid twice daily.
Figure 5A:
FIG. 5A is a picture showing untreated human skin having calluses.
Figure 5B:
FIG. 5B is a picture showing the human skin of FIG. 5A 3 days after treatment with a mixture of corosolic acid, oleanolic acid, and ursolic acid twice daily.
Figure 6A:
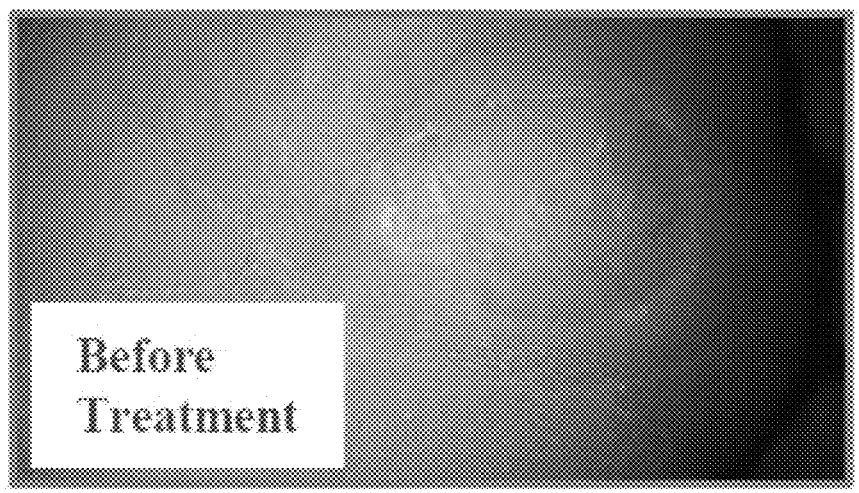
FIG. 6A is a picture showing untreated human skin having calluses.
Figure 6B:
FIG. 6B is a picture showing the human skin of FIG. 6A 5 days after treatment with a methanol extract of *Tecoma stans* twice daily.

Ursolic acid (FIG. 1F, 3β-Hydroxy-12-ursen-28-ic acid, urson, prunol, malol) is another pentacyclic triterpene acid present in many plants. It can be found in fruits and herbs such as apples, basil, bilberries, cranberries, peppermint, rosemary, lavender, oregano, thyme, hawthorn, and prunes. Ursolic acid has been investigated for its potential anticancer effects. In some embodiments, the ursolic acid of the present disclosure is sourced from at least one species of *Tecoma*, preferably from *Tecoma stans*. Alternatively, ursolic acid may be commercially available from vendors such as Sigma-Aldrich, Acros Organics, TCI America, Spectrum Chemicals, and Enzo Life Sciences.

Oleanolic acid (FIG. 1E, oleanic acid) is also a naturally occurring pentacyclic triterpenoid. It can be found in olive oil, *Phytolacca americana* (American pokeweed), *Syzygium* spp, and garlic. Oleanolic acid has been researched for its anti-HIV and anti-HCV activities. In some embodiments, the oleanolic acid of the present disclosure is sourced from at least one species of *Tecoma*, preferably from *Tecoma stans*. Alternatively, oleanolic acid may be commercially available from vendors such as Sigma-Aldrich, Acros Organics, Alfa Aesar, and MP Biomedicals.

The present disclosure also relates to a formulation involving the aforementioned composition, and a pharmaceutically acceptable carrier and/or excipient, wherein corosolic acid, oleanolic acid, and ursolic acid are each present in an amount of 0.01-50 g/L, preferably 0.1-30 g/L, preferably 0.5-20 g/L, preferably 1-15 g/L, preferably 2-10 g/L, preferably 4-7 g/L, relative to a total volume of the formulation.

In one or more embodiments, the pharmaceutically acceptable carrier and/or excipient is at least one selected from the group consisting of an organic solvent, a buffer, an inorganic salt, a fatty acid, a vegetable oil, a synthetic fatty ester, a surfactant, and a polymer.

Suitable organic solvents are as previously specified. In a preferred embodiment, the pharmaceutically acceptable carrier and/or excipient includes DMSO. If present, the organic solvent may be present in the formulation in an amount of 1-1,000 g/L, 10-750 g/L, 25-500 g/L, 50-250 g/L, or 100-200 g/L.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethyl ammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the formulation may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

In a preferred embodiment, the formulation containing the mixture of corosolic acid, oleanolic acid, and ursolic acid is intended for topical application and it may further contain the emulsifier, the emollient, and the occlusive agent as described in the first aspect. If present, the emulsifier may be present in the formulation in an amount of 1-100 g/L, 5-80 g/L, 10-60 g/L, or 15-30 g/L. If present, the emollient may be present in the plant-based composition in an amount of 1-100 g/L, 5-80 g/L, 10-60 g/L, or 15-30 g/L. If present, the occlusive agent may be present in the plant-based composition in an amount of 1-100 g/L, 5-80 g/L, 10-60 g/L, or 15-30 g/L. Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety. In some embodiments, the formulation may be formulated for oral administration.

Another aspect of the present disclosure relates to a method for treating a skin disease or condition. The method involves topically administering an effective amount of the plant-based composition or the formulation containing the mixture of corosolic acid, oleanolic acid, and ursolic acid onto a subject in need of therapy. In one or more embodiment, the skin disease or condition is at least one selected from the group consisting of warts, corns, calluses, umbilical granulomas, and superficial basal cell carcinoma.

Hyperkeratotic tissues such as corns (heloma), calluses (tyloma) and warts (condyloma) are well defined, thickened lesions of the epidermis. Pain produced by the thickened tissue can cause these lesions to be debilitating.

Corns (heloma) and calluses (tyloma) may occur at skin sites that are involved in chronic mechanical stress. Corns are found on skin surfaces, principally on the dorsal surface of toes or fingers and between toes. Corns can be painful when pressed. A hard corn (*Heloma durum*) is a hyperkeratotic lesion which appears over a bony prominence and may have a deep nucleus. A soft corn (*Heloma molle*) is a hyperkeratotic lesion which is frequently found between adjacent toes. A callus may be a diffuse or circumscribed area of hyperkeratosis at a site of repeated pressure and friction. Calluses may be found on the soles of feet, especially metatarsal heads, as well as palms and knees. Calluses are not necessarily painful.

Warts may be caused by skin infection with Human papillomavirus (HPV). Once developed, warts can be spread to other parts of the body or to other persons through skin-to-skin contact or contact with a surface contaminated with HPV. Warts are more commonly diagnosed based on their physical appearances and locations on the body. Various types of wart have been classified by their clinical presentation (e.g. shape, site affected), as well as the type of human papillomavirus involved. Common wart (*Verruca vulgaris*) is a domed, irregularly surfaced lesion that displays hyperkeratosis and may occur, most often on fingers or hands. Periungual wart is a cauliflower-like cluster of warts occur on the skin around finger and toe nails. Flat wart (*Verruca plana*) is a small, smooth wart that usually occurs on the face, neck, hands, wrists and knees. Flat warts are most common on the faces and extremities of children and on the lower legs of women. Plantar wart (*Verruca planlaris*) a hard, sometimes painful lump that is usually only found on the soles of the feet. Plantar warts are often observed with multiple black specks in the center and become callused and grow into the foot due to the forces exerted on the foot from everyday movement. Plantar warts may often be associated with pain.

Umbilical granuloma is a common umbilical abnormality in infants, causing inflammation and drainage. It presents as soft, moist, pink friable lesion on a baby's belly button. It usually appears after the umbilical cord has been cut. It is also possible for an adult to develop an umbilical granuloma.

Basal cell carcinoma (BCC), also known as basal cell cancer, is a common type of skin cancer. BCC often appears as a painless raised area of skin, which may be a shiny, pearly skin nodule. BCC most often affects the skin of head, neck, and trunk that are exposed to the sun. Superficial basal cell carcinoma, formerly referred to in-situ basal cell carcinoma, is characterized by a superficial proliferation of neoplastic basal cells.

As used herein, the terms "treat", "treatment", and "treating" in the context of the administration of the composition to a subject in need thereof refer to the reduction or inhibition of the progression and/or duration of a disease, the reduction or amelioration of the severity of the disease, and/or the amelioration of one or more symptoms thereof resulting from the administration the composition. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease, and relieving the disease (causing regression of the disease). With regard to the disease or condition, these terms simply mean that one or more of the symptoms of the disease or condition will be reduced. Such terms may refer to one, two, three, or more results following the administration of the composition: (1) a stabilization, reduction (e.g. by more than 10%, 20%, 30%, 40%, 50%, preferably by more than 60% of the size of a callus or a corn relative to its initial size before administration), or elimination of the symptoms (e.g. removal of a wart), (2) inhibiting the growth of pathogens (e.g. HPV), (3) relieving to some extent one or more symptoms associated with the disease or condition (e.g. reduction in pain, redness, bumpiness, swelling, and/or oozing associated with warts and umbilical granuloma), (4) an increase in disease-free, relapse-free, progression-free duration, or rate, (5) a decrease in hospitalization rate, and (6) a decrease in hospitalization length.

The term "subject in need of therapy", "subject", and "patient" are used interchangeably. As used herein, they refer to any subject for whom or which therapy, including with the according to the present disclosure compositions (e.g. the plant-based composition, the formulation containing the mixture of corosolic acid, oleanolic acid, and ursolic acid) is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human. In some embodiment, the subject is an infant.

The method involves topically administering an effective amount of the plant-based composition or the formulation containing the mixture of corosolic acid, oleanolic acid, and/or ursolic acid onto the subject. In some embodiments, the subject is administered with an effective amount of the plant-based composition or the formulation at least once daily, 2 to 10 times daily, or 3 to 5 times daily for at least 1 day, 2 to 30 consecutive days, 5 to 21 consecutive days, or 7 to 14 consecutive days. During administration, the plant-based composition or the formulation may be applied, rubbed, and/or spread onto the desired/affected area of skin. Preferably, the desired/affected area of skin is cleaned prior to administration.

The terms "effective amount", "therapeutically effective amount", or "pharmaceutically effective amount" refer to that amount of the composition being administered which will relieve to some extent one or more of the symptoms of the disease being treated. The result can be reduction and/or alleviation of the signs, symptoms, or causes of a disease, or any other desired alteration of a biological system. The amount will vary with the condition being treated and the concentration of the active ingredients (e.g. the alcohol extract of at least one species of Tecoma, the mixture of corosolic acid, oleanolic acid, and/or ursolic acid) present in the formulation being administered. Appropriate amounts in any given instance will be readily apparent to those of ordinary skill in the art by routine experimentation.

Figure 7A:
FIG. 7A is a picture showing untreated infant skin having umbilical granulomas.
Figure 7B:
FIG. 7B is a picture showing the infant skin of FIG. 7A 3 days after treatment with a methanol extract of *Tecoma stans* twice daily.

Experiments were carried out which evaluate the effectiveness of the plant-based composition and the formulation containing the mixture of corosolic acid, oleanolic acid, and ursolic acid on treating warts (see FIGS. 2A-C, 3A-C, and 4A-C), corns and calluses (see FIGS. 5A-B, and 6A-B) and umbilical granuloma (see FIGS. 7A-B). It is worth noting that the combination of three acids, namely corosolic acid, oleanolic acid, and ursolic acid, has a synergistic effect for treatment of the aforementioned skin lesions compared to topical application of only one acid among the three (see Example 1).

The compositions and formulations of the present disclosure may also be used in the treatment of hyperkeratinizing and hyperproliferative skin diseases and conditions including, but not limited to, melanoma, basal cell carcinoma (BCC), psoriasis, viral infection caused by the herpes simplex virus (e.g. cold sores), nail deformations (e.g. ingrown toenails), mouth ulcers (canker sores), ichthyoses, porokeratoses, follicular keratoses, palmoplantar keratodermas, eczema, acne, dandruff, and dry skin.

A further aspect of the present disclosure relates to a personal care product comprising the plant-based composition or the composition/formulation containing the mixture of corosolic acid, oleanolic acid, and ursolic acid. As used herein, the term "care" refers to the improvement and/or the maintenance of the qualities of the skin. These qualities are subject to improvement and/or are maintained through care of the skin both in healthy subjects as well as those which present diseases and/or conditions of the skin, such as and not restricted to, warts, corns, calluses, umbilical granulomas, and superficial basal cell carcinoma. Exemplary personal care products include plasters, bandages, patches, wound healing ointments, sunscreens, body lotions, facial creams, body wash, facial wash, bar soap, liquid soap (e.g., hand soap), hand sanitizer (including rinse off and leave-on and aqueous-based hand disinfectants), antiperspirants, deodorants, shampoos, infant care products (e.g. infant body lotions, creams, and body washes), dental care products such as toothpastes and mouth wash.

The examples below are intended to further illustrate protocols for preparing, characterizing the plant-based composition as well as the composition/formulation containing the mixture of corosolic acid, oleanolic acid, and ursolic acid, and uses thereof, and are not intended to limit the scope of the claims.

Example 1

Experimental

Initial steps involved extracting Tecoma stans leaves with methanol or ethanol alcohol. Then, the extract was obtained via evaporating the alcohol and re-suspending the dry matter in pure DMSO (dimethylsulphoxide) at a concentration of 20 mg/mL DMSO. Importantly, active ingredients were found mainly in the leaves of the plant, and only minimum curing effect was found using ethanolic or methanolic extract from Tecoma stans flowers, roots, or fruit (also known as pods). Stem and bark of Tecoma stans showed only very minor therapeutic effect compared to the leaf extract (20%).

As disclosed herein, 14 compounds have been isolated from dry leaves of Tecoma stans, four of which are known for their antidiabetic effect and ability to reduce the glycemic index. After identifying the 14 compounds in the methanolic extract from the dry leaves, each compound was independently tested on human skin warts.

A minor curing effect was observed by applying corosolic acid (FIG. 1I). Therefore, corosolic acid was mixed with its two related compounds, namely oleanolic acid (FIG. 1E) and ursolic acid (FIG. 1F), isolated from the same extract. Compositions containing a mixture of these three compounds were prepared by mixing the compounds in an ointment at a concentration of 1 mg/gm of each compound per a total weight of the ointment, emulsifying the compounds in a lotion base at a concentration of 0.1 mg/mL of each compound per a total volume of the lotion, or suspending three compounds together in DMSO at a concentration of 1 mg/mL of each compound per a total volume of DMSO. The compositions were applied topically twice a day to the desired skin area as indicated in each case (see FIGS. 3A-C, 4A-C, 5A-B).

Compositions containing the mixture of corosolic acid, oleanolic acid, and ursolic acid were able to cure skin warts, with an efficacy that was only about 10% less than that of the crude methanolic extract of Tecoma stans leaves. Therefore, a combination of the three compounds including oleanolic acid, ursolic acid, and corosolic acid played a major role in the anti-wart activity of Tecoma stans. It is important to note that none of the three compounds showed anti-wart activity alone that exceeded 10% of the crude methanol extract. Accordingly, obtaining 90% effectiveness rate of the crude methanol extract by combining corosolic acid, oleanolic acid, and ursolic acid indicated a synergistic curing effect among the three compounds. It is also important to note that mixing the three compounds together in DMSO yielded faster therapeutic results than the topical cream that contained same concentrations of the three compounds. Similarly, three other structurally related heterocyclic compounds were tested for their ability to kill various melanoma cell lines by induction of apoptosis.

Example 2

Results and Discussions

Our experimental data showed that certain extracts prepared from Tecoma stans as well as some of its isolated and characterized compounds were able to treat skin warts, skin callus, skin corns and umbilical granulomas.

Interestingly, when the crude extracts and certain combinations of the isolated 14 compounds (see FIGS. 1A-N) were used as topical ointments, they were able to effectively cure skin warts, callus, and corns without signs of recurrence, indicating that they were able to eradicate the causative papilloma virus. Specifically, mixtures of three natural heterocyclic compounds (i.e. corosolic acid, oleanolic acid, and ursolic acid) which were isolated from a *Tecoma stans* plant have been shown to effectively treat skin wart, callus, corns, and umbilical granuloma. These compounds are harmless on humans, and cause no skin irritations.

In addition, the experimental data of treating umbilical granuloma using extracts from *Tecoma stans* showed effective removal of the granuloma within two days using the topical application twice per day. It is worth noting that neither the tested extracts nor the pure compounds isolated from *Tecoma stans* caused any skin reaction or left any scar on the entire group of tested subjects. These data indicated that extracts from *Tecoma stans* and its purified and identified compounds were effective for treating skin wars, callus, corn, and umbilical granuloma. Furthermore, the data demonstrated that the extract from *Tecoma stans* might be used to treat herpes simplex virus including type 1 (HSV-1) and type 2 (HSV-2). Therefore, these data collectively indicated that extracts from *Tecoma stans* contain therapeutic compounds with antiviral activity (including anti-HSV-1, anti-HSV-2, and anti-papilloma virus activities).

Example 3

Clinical Impact

Based on the above, this disclosure provides natural crude extracts as well as isolated compounds from *Tecoma stans* and potentially other *Tecoma* species useful for treating skin warts, skin callus, skin corns, and umbilical granulomas, potentially for treating genital warts and superficial basal cell carcinomas, and being applied as an antiviral agent for treating papilloma virus and HSV-1 and HSV-2 viruses.

The invention claimed is:

1. A plant-based composition, comprising:
    1-500 g/L of an alcohol extract of at least one species of *Tecoma* relative to a total volume of the plant-based composition; and
    an exogenous pharmaceutically acceptable carrier and/or excipient which is not present in the at least one species of *Tecoma*,
    wherein the alcohol extract of the at least one species of *Tecoma* is sourced from a leaf,
    wherein the exogenous pharmaceutically acceptable carrier and/or excipient is DMSO,
    wherein the alcohol extract of the at least one species of *Tecoma* is obtained by extracting the leaf of the at least one species of *Tecoma* with an alcohol at a temperature of 10-50° C., and
    wherein the plant-based composition is obtained by re-suspending the alcohol extract of at least one species of *Tecoma* in DMSO.

2. The plant-based composition of claim 1, wherein the at least one species of *Tecoma* is selected from the group consisting of *Tecoma beckii, Tecoma capensis, Tecoma castanifolia, Tecoma cochabambensis, Tecoma fulva, Tecoma nyassae, Tecoma rosifolia, Tecoma stans, Tecoma tenuiflora,* and *Tecoma weberbaueriana*.

3. The plant-based composition of claim 2, wherein the at least one species of *Tecoma* is *Tecoma stans*.

4. The plant-based composition of claim 1, wherein the alcohol extract of at least one species of *Tecoma* is a methanol extract, an ethanol extract, or both.

5. The plant-based composition of claim 1, comprising 10-100 g/L of an alcohol extract of *Tecoma stans* relative to a total volume of the plant-based composition.

6. A personal care product, comprising the plant-based composition of claim 1.

7. The plant-based composition of claim 1, wherein the alcohol extract of at least one species of *Tecoma* is obtained by extracting the at least one species of *Tecoma* with an alcohol at a temperature of 20-30° C.

8. The plant-based composition of claim 1, wherein the alcohol extract of at least one species of *Tecoma* is a methanol extract.

9. A plant-based composition, comprising:
    1-50 mg/mL of an alcohol extract of leaves of at least one species of *Tecoma* relative to a total volume of the plant-based composition; and
    DMSO,
    wherein the plant-based composition is obtained by:
        extracting the leaves of the at least one species of *Tecoma* with methanol at a temperature of 10-50° C. to form a methanol extract,
        drying the methanol extract to form a dried methanol extract, then
        re-suspending the dried methanol extract in DMSO, and
    wherein the plant-based composition exhibits an anti-wart efficacy that is at least 10% greater than that of a comparative formulation comprising oleanolic acid, ursolic acid, and corosolic acid.

10. The plant-based composition of claim 9, which comprises 20 mg/mL of the alcohol extract of leaves of at least one species of *Tecoma* relative to a total volume of the plant-based composition.

* * * * *